United States Patent [19]

DeLuca et al.

[11] 4,254,045

[45] Mar. 3, 1981

[54] 1α-HYDROXY-2β-FLUOROCHOLECAL-CIFEROL

[75] Inventors: Hector F. DeLuca, Madison, Wis.; Nobuo Ikekawa, Tokyo, Japan; Yoko Tanaka, Madison, Wis.; Masuo Morisaki, Tokyo, Japan; Jun-ichi Oshida, Tokyo, Japan

[73] Assignee: Wisconsin Alumni Research Foundation, Madison, Wis.

[21] Appl. No.: 142,552

[22] Filed: Apr. 21, 1980

[51] Int. Cl.$^3$ .............................................. C07J 9/00
[52] U.S. Cl. ........................ 260/397.2; 260/239.55 R
[58] Field of Search ....................................... 260/397.2

[56] References Cited

U.S. PATENT DOCUMENTS

| 3,741.996 | 6/1973 | DeLuca et al. | 260/397.2 |
| 4,046,760 | 9/1977 | Jones et al. | 260/239.55 R |

*Primary Examiner*—Elbert L. Roberts
*Attorney, Agent, or Firm*—Howard W. Bremer

[57] ABSTRACT

The invention provides new derivatives of vitamin $D_3$, specifically, 1α-hydroxy-2β-fluorocholecalciferol.

The compound is characterized by vitamin D-like activity as measured by its ability to stimulate intestinal calcium transport, mobilize calcium from bone, increase serum inorganic phosphorous and in their antirachitic acitivity. The compound could, therefore, find ready application as a substitute for vitamin D in its various known applications and in the treatment of various metabolic bone diseases.

9 Claims, No Drawings

1α-HYDROXY-2β-FLUOROCHOLECALCIFEROL

Technical Field

The invention described herein was made in the course of work under a grant or award from the Department of Health, Education, and welfare.

DESCRIPTION

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin is first hydroxylated in the liver to form 25-hydroxy vitamin $D_3$ and is further hydroxylated in the kidney to produce 1α,25-dihydroxy vitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

BACKGROUND ART

References to various of vitamin D derivatives are extant in the patent and other literature. See, for example, U.S. Pat. Nos: 3,565,924 directed to 25-hydroxycholecalciferol; 3,697,559 directed to 1,25-dihydroxycholecalciferol; 3,741,996 directed to 1α-hydroxycholecalciferol; 3,907,843 directed to 1α-hydroxyergocalciferol; 3,715,374 directed to 24,25-dihydroxycholecalciferol; 3,739,001 directed to 25,26-dihydroxycholecalciferol; 3,786,062 directed to 22-dehydro-25-hydroxycholecalciferol; 3,847,955 directed to 1,24,25-trihydroxycholecalciferol; 3,906,014 directed to 3-deoxy-1α-hydroxycholecalciferol; 4,069,321 directed to the preparation of various side chain fluorinated vitamin $D_3$ derivatives and side chain fluorinated dihydrotachysterol$_3$ analogs.

DISCLOSURE OF INVENTION

A new derivative of vitamin $D_3$ has been prepared which expresses excellent vitamin D-like activity as measured by its ability to stimulate intestinal calcium transport, in its ability to mobilize calcium from bone, in its ability to increase serum inorganic phosphorus and in its antirachitic activity as measured by the rat line test. Such compound, therefore, could serve as a substitute for vitamin D in its various known applications and would be useful in the treatment of various metabolic bone diseases.

This derivative has been identified as 1α-hydroxy-2β-fluorocholecalciferol (1α-OH-2βF-cholecalciferol, 1α-OH-2βF-vitamin $D_3$ or 1α-OH-2βF-$D_3$).

BEST MODE FOR CARRYING OUT THE INVENTION

The compound of this invention was synthesized in accordance with the following description (in which all temperatures indicated are in °C.) and abbreviated schematic:

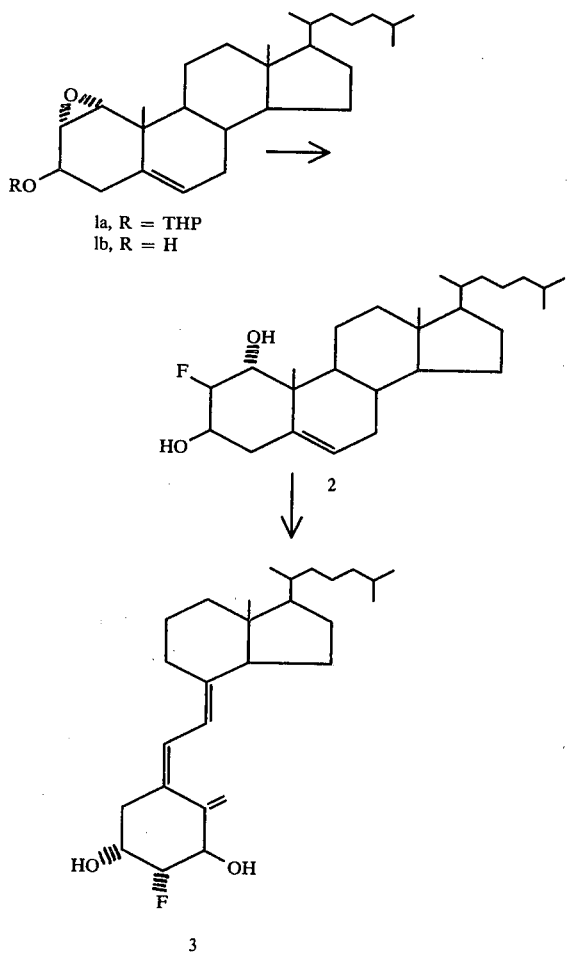

1a, R = THP
1b, R = H

Treatment of 1a(1,2α-epoxycholest-5-en-3β-yl tetrahydropyranyl ether) with pyridinium p-toluenesulfonate (0.1 mol equiv.) in a 1:1 mixture of $CH_2Cl_2$ and MeOH at 55° for 5 hr gave the epoxyalcohol 1b (75% yield, mp 105°–107°, δ 0.72 (3H, s, 18-Me), 1.15 (3H, s, 19-Me), 3.08 and 3.20 (2H, a pair of d, J=4 Hz, 1- and 2-H), 3.90 (1H, m, 3-H), 5.5 (1H, m, 6-H), m/e 400 (M+) 382, 342, 287, 269). (The starting material 1a is readily obtainable in accordance with the procedure of M. Morisaki, A. Saika, K. Bannai, M. Sawamura, J. R. Lightbourn and N. Ikekawa, Chem. Pharm. Bull., 23, 3272 (1975).

Attempts to introduce fluorine at C-2 of 1b by Et$_4$NF or KF/dicyclohexyl-18-crown-6 were fruitless. However, heating of 1b with potassium hydrogen difluoride (Merck KF cont. KHF$_2$) in ethylene glycol at 170° for 1.5 hr furnished the fluorohydrin 2 (48% yield, mp 167°–170°, δ 0.68 (3H, s, 18-Me), 1.13 (3H, s, 19-Me), 3.7 (1H, m, 3-H), 3.96 (1H, m, 1-H), 4.78 (1H, td, $J_{HF}$=50 Hz, $J_{HH}$=3 Hz, 2-H), 5.6 (1H, m, 6-H), m/e 420 (M+), 405, 402, 400, 382, 307, 289, 265, 247). (See P. A. Grieco, T. Sugahara, Y. Yokoyama and E. Williams, J. Org. Chem., 44, 2189 (1979).) The β orientation of the fluorine at C-2 was predicted from diaxial opening of epoxide and evidenced with the coupling constant (3 Hz) of the triplet of doublets in 2 which is consistent with dihedral angles of θ ($H_2-H_1$)=θ($H_2-H_3$)=60°.

Transformation of 2 into 2β-fluoro-1α-hydroxyvitamin D3(3) was carried out by the standard vitamin D methodology. Thus, acetylation of 2 with acetic anhydridepyridine at 90° for 4 hr gave the diacetate which on bromination (N-bromosuccinimide in refluxing $CCl_4$ for 1.3 hr) followed by dehydrobromination (s-collidine in refluxing xylene for 15 min) was converted to a mixture of the 5,7-diene and 4,6-diene. Acid treatment (p-toluene-sulfonic acid in acetone, overnight) of the crude product converted the 4,6-diene into a much less polar material to allow for effective isolation by chromatography of the desired 5,7-diene (30% yield from 2, $\lambda_{max}$ 262, 271, 281.5 and 293 nm). This was irradiated with a medium pressure mercury lamp (Hanovia 654A 36; 200W) in a mixture of benzene-EtOH (2:1) at 0° for 2.5 min and then refluxed for 1 hr to give, after purification by silica gel TLC developed 2 times with benzene-AcOEt (14:1), the vitamin D diacetate in 36% yield. Subsequent saponification with 2.5% KOH in a mixture of MeOH-THF (1:1) at 15° overnight and then purification by HPLC (Zorbax SiL, 15 cm×4.1 mm, $CH_2Cl_2$-hexane (4:1), 90 kg/$cm^2$) afforded 2β-fluoro-1α-hydroxyvitamin $D_3$ (3) ($\lambda_{min}$ 226, $\lambda_{max}$ 265 nm, m/e 418 (M+), 403, 400, 398, 380, 365, 305, 287, 150, 135, δ 0.49 (3H, s, 18-Me), 0.82 (6H, d, J=7 Hz, 26,27-Me), 0.87 (3H, d, J=6 Hz, 21-Me), 4.3 and 4.5 (3H, a pair of m, 1-, 2- and 3-H), 5.14 and 5.54 (2H, a pair of m, 19-H), 5.99 (1H, d, J=12 Hz, 7-H), 6.36 (1H, d, J=12 Hz, 6-H). The mass spectrum of 3 revealed only weak ion due to cleavage of C-7,8 bond (m/e 170) and instead, m/e 380 derived from M—$H_2O$—HF predominated. It should also be noted that the fluorine atom has a remarkable effect of decreasing polarity and the retention time of 3 on HPLC (wide supra) was 4.1 min, when those of 1α-hydroxyvitamin $D_3$ and vitamin $D_3$ were 11.0 and 1.5 min, respectively.)

If it is desired for certain purposes the acetylated 5,7-diene product derived from the acetylation of 2 as previously described can be saponified by well known means (5% KOH in MeOH, 20° C., 15 hours) to convert the acetoxy group at the 3-position to hydroxyl.

Also, if desired the previtamin compound may be recovered either before or after saponification of the acetyl group or groups present, by evaporation of the solvent medium followed by chromatography on silica gel, as is well known in the art, and subsequently converted to the vitamin compound. The previtamin compound can be convenveniently depicted by the following formula

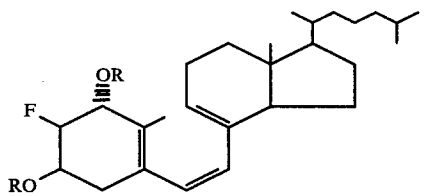

The vitamin D derivative of this invention, 1α-hydroxy-2β-fluorocholecalciferol, can be obtained in crystalline form by recrystallization from a suitable solvent or solvent system, e.g. ethanol.

BIOLOGICAL ACTIVITY

The biological potency of 1α-OH-2βF-$D_3$ was confirmed by appropriate in vivo assays in rats.

Male weanling rats (purchased from Holtzman Co., Madison, Wisconsin) were fed ad libtum water and either a low-calcium-adequate phosphorous, vitamin D deficient diet as described by Suda et al (J. Nutrition 100, 1049, 1970) or a high calcium-low phosphorous, vitamin D deficient diet (richitogenic dient) as described by Tanaka and DeLuca (PNAS 71 1040, 1974) for three weeks.

MEASUREMENT OF SERUM INORGANIC PHOSPHOROUS

Rats that had been fed the rachitogenic diet for three weeks were divided into six groups of 5-6 rats each and were given, respectively, 325 pmole of either 1α-OH-2βF-$D_3$ or 1αOH$D_3$ dissolved in 0.05 ml of 95% ethanol intrajugularly either 24 hours or 96 hours prior to sacrifice. The rats in control groups were given the ethanol vehicle only in the same manner. They were killed by decapitation at the indicated times after dose and blood was collected.

Blood was centrifuged immediately to yield serum. Ten percent trichloroacetic acid was added to the serum, and the supernatant recovered after centrifugation was analyzed by the method as described by P. S. Chen et al (Anal. Chem. 28, 1756, 1956). Results are shown in Table I.

TABLE I

Increase in serum inorganic phosphorous concentration in response to a single dose of 325 pmole either 1α-OH-2βF-$D_3$ or 1α-OH-$D_3$.

| Compound Given | Concentration of Serum 24 hrs. after dose | Inorganic Phosphorous 96 hrs. after dose |
|---|---|---|
| Ethanol | 1.6 ± 0.4*[a] | 1.4 ± 0.4[d] |
| 1α-OH-2βF-$D_3$ | 3.3 ± 0.4[b] | 2.4 ± 0.3[e] |
| 1α-OH-$D_3$ | 2.6 ± 0.4[c] | 1.9 ± 0.2[f] |

*standard deviation of the mean
Significance of difference
[b]from [a]p<0.001
[c]from [a]p<0.005
[b]from [c]p<0.025
[e]from [d]p<0.001
[f]from [d]p<0.05
[e]from [f]p<0.025

INTESTINAL CALCIUM TRANSPORT

Rats that had been fed the low calcium-vitamin D deficient diet for three weeks were divided into four groups of 5-6 rats each and were given respectively 32.5 pmole, 68 pmole or 325 pmole of 1α-OH-2βF-$D_3$ dissolved in 0.05 ml 95% ethanol intrajugularly 24 hours prior to sacrifice. The rats in the control group were given the ethanol vehicle only in the same manner. They were killed by decapitation and their duodena were then immediately removed to measure the intestinal calcium transport activity by the method described by Martin and DeLuca (Am. J. Physiol. 216, 1351, 1969). Results are shown below in Tabe 2, second column.

TABLE 2

Increase in serum calcium concentration and in intestinal calcium transport activity in response to a single dose of $1\alpha$-OH-$2\beta$F-$D_3$ or $1\alpha$-OH-$D_3$ given 24 hours prior to sacrifice.

| Compound Given | Amount of Compound (pmole) | Serum Calcium Concentration (mg/100 ml) | Intestinal Calcium Transport - $^{45}$Ca serosal/$^{45}$Ca mucosal |
|---|---|---|---|
| Ethanol | | 4.8 ± 0.1*[a] | 5.0 ± 1.3[a] |
| $1\alpha$OH-$2\beta$F-$D_3$ | 32.5 | 5.6 ± 0.3[b] | 7.2 ± 1.0[b] |
| | 68.0 | 6.5 ± 0.3[b] | 9.2 ± 2.2[b] |
| | 325 | 6.2 ± 0.3[b] | 8.8 ± 1.8[b] |
| $1\alpha$OH-$D_3$ | 32.5 | 5.5 ± 0.1[b] | — |
| | 68.0 | 6.0 ± 0.4[b] | — |
| | 325 | 6.2 ± 0.1[b] | — |

Significance of difference
[b]from [a]p<0.001
[b]from [a]p<0.001

Another measurement of the activation of intestinal calcium transport by $1\alpha$-OH-$2\beta$F-$D_3$ was obtained using rats that had been fed the rachitogenic diet for three weeks. They were divided into five groups of 5–6 rats each and were given respectively either 6.5 pmol/day or 65 pmole/day of either $1\alpha$-OH-$2\beta$F-$D_3$ or $1\alpha$-OH-$D_3$ dissolved in 0.05 ml 5% ethanol - 95% propylene glycol mixture, subcutaneously daily for seven days. Twenty hours after the last dose, they were killed by decapitation, their blood was collected for measurement of concentration of serum inorganic phosphorous. Their duodena were used for measurement of intestinal calcium transport activity, respectively, as described above. The results are shown in Table 3, first column. Increase of serum phosphorous concentration in response to a daily dose of the compound is shown in Table 3, second column.

ANTIRACHITIC ACTIVITY

Rats that had been fed the rachitogenic diet were divided into five groups of 5–6 rats each and were given either 6.5 pmole/day or 65 pmole/day of either $1\alpha$-OH-$2\beta$F-$D_3$ or $1\alpha$-OH-$D_3$ dissolved in 0.05 ml 5% ethanol - 95% propylene glycol mixture for seven days as described above. Rats in the control group received the vehicle only in the same manner. A week later, the rats were killed and their duodena were used for measurement of intestinal calcium transport activity and their blood was used for measurement of serum inorganic phosphorous as previously described with results as shown in Table 3, first and second columns respectively. Their radii and ulnae were removed and evaluated in accordance with the rat line test (U.S. Pharmacopoeia, 15th Ed., Mack Publishing Co., Easton, Pa. 1955, p. 889). Results are shown in Table 3, third column.

TABLE 3

Intestinal calcium transport and increase in serum inorganic phosphorous concentration in response to and the antirachitic activity of daily dose of $1\alpha$-OH-$2\beta$F-$D_3$ or $1\alpha$-OH-$D_3$.

| Compound Given | Amount of Compound (pmole/day) | Intestinal Calcium Transport $^{45}$Ca serosal/$^{45}$Ca mucosal | Serum Inorganic Phosphorous (mg/100 ml) | Antirachitic Activity (Unit) |
|---|---|---|---|---|
| Ethanol | | 2.7 ± 0.4*[a] | 2.6 ± 0.5[f] | 0 |
| $1\alpha$-OH-$2\beta$F-$D_3$ | 6.5 | 6.1 ± 1.2[b] | 3.4 ± 1.0[g] | 1 |
| | 65 | 13.9 ± 3.4[c] | 5.1 ± 0.7[h] | >5 |
| $1\alpha$-OH-$D_3$ | 6.5 | 4.8 ± 0.9[d] | 3.0 ± 0.4[g] | 1 |
| | 65 | 9.2 ± 0.8[e] | 4.5 ± 0.7[i] | 4–5 |

*Standard deviation of the mean
Significance of difference
[d]from [a]p<0.005
[b,c], [e]from [a]p<0.001
[e]from [c]p<0.025
[g]from [f]N.S.
[h], [i]from [f]p<0.005
[h]from [i]N.S.

BONE CALCIUM MOBILIZATION

Rats that had been fed the low calcium, vitamin D deficient diet of Suda et al for three weeks were divided into seven groups of 5–6 rats each and were given respectively either 32.5 pmole, 68.0 pmole or 325 pmole of either $1\alpha$-OH-$2\beta$F-$D_3$ or $1\alpha$-OH-$D_3$ dissolved in 0.05 ml 95% ethanol intrajugularly 24 hours prior to sacrifice. The rats in the control group were given the ethanol vehicle in the same manner. The rats were killed by decapitation and the blood was collected. The blood was centrifuged to obtain serum. One tenth ml of serum was mixed with 1.9 ml of 0.1% lanthanum chloride solution and the calcium concentration was measured with an atomic absorption spectrophotometer (Perkin-Elmer Model 214). As intake of calcium from the diet is negligibly low, increase of serum calcium concentration in response to $1\alpha$-OH-$2\beta$F-$D_3$ is presumed to reflect the bone calcium mobilization ability of the compound. The results are shown in Table 2, first column.

It is evident from the foregoing data that $1\alpha$-OH-$2\beta$F-$D_3$ exhibits pronounced vitamin D-like activity and appears to be wholly as effective in this regard as $1\alpha$-OH-$D_3$ (see U.S. Pat. No. 3,741,996).

We claim:

1. Compounds having the formula where each of R and R₁ is hydrogen or acetyl.

2. The compound of claim 1 wherein R and R₁ are hydrogen.

3. The compound of claim 2 in crystalline form.

4. Compounds having the formula where R and R₁ are hydrogen or acetyl.

5. The compound of claim 4 where R and R₁ are hydrogen.

6. Compound having the formula where R and R₁ are hydrogen or acetyl.

7. The compound of claim 6 where R and R₁ are hydrogen.

8. Compounds having the formula where R and R₁ are hydrogen or acetyl.

9. The compound of claim 1 where R and R₁ are hydrogen.

UNITED STATES PATENT OFFICE
CERTIFICATE OF CORRECTION

Patent No. 4,254,045      Dated March 3, 1981

Inventor(s) Hector F. DeLuca et al

It is certified that error appears in the above-identified patent and that said Letters Patent are hereby corrected as shown below:

Add the following paragraph as the first paragraph of the specification:

--The invention described herein was made in the course of work under a grant or award from the Department of Health, Education, and Welfare, and U.S. Japan Cooperative Grant INT-76-05793 and IPA No. 0001 awarded by the National Science Foundation.--

Signed and Sealed this

Twenty-sixth Day of May 1981

[SEAL]

*Attest:*

RENE D. TEGTMEYER

*Attesting Officer*     *Acting Commissioner of Patents and Trademarks*

UNITED STATES PATENT OFFICE
CERTIFICATE OF CORRECTION

Patent No. 4,254,045　　　　　　　Dated March 3, 1981

Inventor(s) Hector F. DeLuca et al

It is certified that error appears in the above-identified patent and that said Letters Patent are hereby corrected as shown below:

In Column 5, Table 3, footnote, after "$^{b}$, $^{c}$, $^{e}$ from $^{a}$ p<0.001" insert -- b) from d) N.S. --

Signed and Sealed this

Twenty-third Day of June 1981

[SEAL]

Attest:

RENE D. TEGTMEYER

Attesting Officer　　　Acting Commissioner of Patents and Trademarks

UNITED STATES PATENT AND TRADEMARK OFFICE
CERTIFICATE OF CORRECTION

PATENT NO. : 4,254,045

DATED : March 3, 1981

INVENTOR(S) : Hector F. DeLuca et al

It is certified that error appears in the above-identified patent and that said Letters Patent is hereby corrected as shown below:

The formula in claim 1 should be changed from 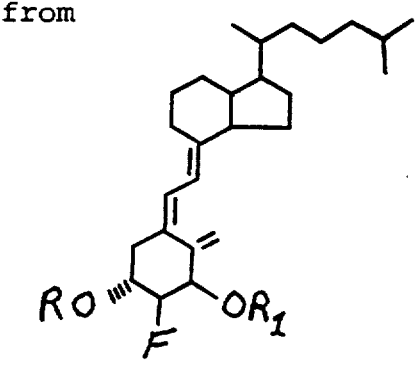  to 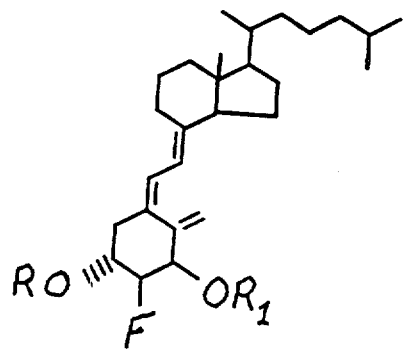

Signed and Sealed this

Twenty-third Day of June, 1992

Attest:

DOUGLAS B. COMER

Attesting Officer

Acting Commissioner of Patents and Trademarks